United States Patent [19]

Cox et al.

[11] 4,086,272

[45] Apr. 25, 1978

[54] PHENYL-ALKANOLAMINE, ALKYLAMINE AND ALPHA-AMINOALKYL KETONE DERIVATIVES AS HEART STIMULANTS

[75] Inventors: David A. Cox, Canterbury; Ian T. Barnish, Ramsgate; Anthony G. Evans, Westgate-on-Sea, all of England

[73] Assignee: Pfizer Inc., New York, N.Y.

[21] Appl. No.: 691,994

[22] Filed: Jun. 2, 1976

Related U.S. Application Data

[62] Division of Ser. No. 443,034, Feb. 15, 1974, Pat. No. 3,976,783, which is a division of Ser. No. 160,529, Jul. 7, 1971, Pat. No. 3,816,516.

[30] Foreign Application Priority Data

Jul. 18, 1970 United Kingdom ............... 34931/70

[51] Int. Cl.$^2$ .................. C07C 103/29; C07C 103/38; A61K 31/165
[52] U.S. Cl. ............................ 260/559 D; 260/558 S; 260/558 A; 260/559 T; 260/559 A; 260/562 P; 260/501.17; 424/324
[58] Field of Search ........... 260/559 A, 559 D, 562 P, 260/562 A, 558 S, 558 A, 501.17, 559 T

[56] References Cited

U.S. PATENT DOCUMENTS

| | | | |
|---|---|---|---|
| 2,661,373 | 12/1953 | Kütz et al. | 260/570.6 |
| 3,056,836 | 10/1962 | Moed | 260/570.6 X |
| 3,278,601 | 10/1966 | Moed | 260/570.6 |
| 3,410,901 | 11/1968 | Kunz et al. | 260/570.7 OH |
| 3,689,524 | 9/1972 | Jack et al. | 260/553 A X |
| 3,723,524 | 3/1973 | Augstein et al. | 260/559 A X |
| 3,843,725 | 10/1974 | Pinhas | 260/570.6 X |
| 3,845,123 | 10/1974 | Cox et al. | 260/562 P |
| 3,872,147 | 3/1975 | Koppe et al. | 260/559 A X |
| 3,873,620 | 3/1975 | Pinhas | 260/570.6 X |
| 3,892,799 | 7/1975 | Pinhas | 260/570.6 X |
| 3,933,911 | 1/1976 | Main | 260/559 A X |
| 3,959,359 | 5/1976 | Pinhas | 260/570.6 X |
| 3,969,410 | 7/1976 | Mentrup et al. | 260/570.6 |
| 3,976,695 | 8/1976 | Kaiser et al. | 260/570.6 |
| 3,979,456 | 9/1976 | Pinhas | 260/570.6 X |
| 4,000,193 | 12/1976 | Lunts et al. | 260/559 A X |

*Primary Examiner*—Daniel E. Wyman
*Assistant Examiner*—Thomas A. Waltz
*Attorney, Agent, or Firm*—Connolly and Hutz

[57] ABSTRACT

Novel substituted 1-phenyl-2-alkylamino-alkanols, 1-phenyl-2-alkylamino-alkanes and α-aminoalkyl phenyl ketones useful as heart stimulants are disclosed.

12 Claims, No Drawings

PHENYL-ALKANOLAMINE, ALKYLAMINE AND ALPHA-AMINOALKYL KETONE DERIVATIVES AS HEART STIMULANTS

CROSS REFERENCE TO RELATED APPLICATIONS

This application is a division of application Ser. No. 443,034 filed Feb. 15, 1974 and now U.S. Pat. No. 3,976,783 which is a division of application Ser. No. 160,529 filed July 7, 1971 and now U.S. Pat. No. 3,816,516.

BACKGROUND OF THE INVENTION

This invention relates to alkanolamine, alkylamine and aminoalkylketo derivatives having useful therapeutic properties. It is particularly concerned with novel substituted 1-phenyl-2-alkylaminoalkanols, 1-phenyl-2-alkylaminoalkanes and α-aminoalkyl phenyl ketones which are β-agonists, i.e. stimulate the β-adrenergic receptors. In particular, these compounds increase the force of myocardial contraction, and are useful in the curative or prophylactic treatment of cardiac conditions such as congestive heart failure. By virtue of their β-receptor stimulating properties these compounds are also useful in the treatment of obstructive airways disease and peripheral vascular disease.

SUMMARY OF THE INVENTION

The compounds of the invention are those having the general formula:

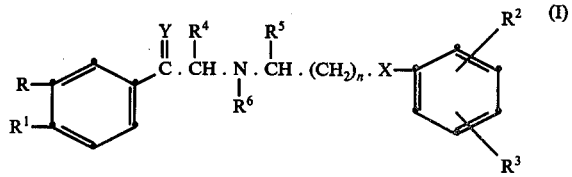

wherein R and $R^1$ are each hydrogen or hydroxy with the proviso that at least one is hydroxy; $R^2$ is hydrogen, alkyl of from 1 to 4 carbon atoms or alkoxy of from 1 to 4 carbon atoms; $R^3$ is acylamino, alkoxycarbonylamino of from 1 to 4 carbon atoms, amoyl or ureido, any one of which may be separated from the phenyl ring by a methylene or ethylene group; $R^4$, $R^5$, and $R^6$ are each hydrogen or alkyl of from 1 to 4 carbon atoms; X is oxygen, sulfur, imino or a direct link; Y is hydrogen and hydroxy, two hydrogens or oxygen; $n$ is 1 to 3 when X is other than a direct link and is 0 to 4 when X is a direct link; and the carboxylic acid esters and aldehyde condensation products of such a compound and the pharmaceutically-acceptable acid addition salts.

In this specification "halogen" comprises fluorine, chlorine, bromine and iodine; "imino" group indicates the group —$NR^7$— where $R^7$ represents hydrogen or a lower alkyl group; and the term "lower" used to qualify an alkyl or alkoxy group, indicates that such group contains up to 4 carbon atoms.

The aldehyde condensation products of the compounds of the invention are oxazolidines, having the formula:

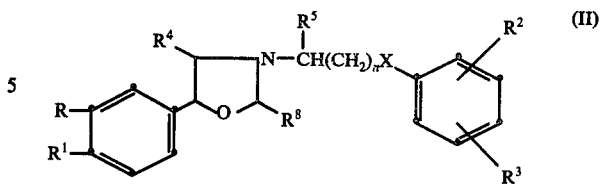

which are formed by condensation of compounds of the invention in which $R^6$ is hydrogen and Y represents a hydrogen atom and a hydroxy group with an aldehyde of the formula $R^8CHO$, where $R^8$ is hydrogen or a lower alkyl group.

DETAILED DESCRIPTION OF THE INVENTION

In the above formulae, when $R^3$ is amoyl, it may be a carbamoyl or sulfamoyl group having the formula —$CO.NR^9R^{10}$ or —$SO_2.NR^9R^{10}$, respectively, where $R^9$ and $R^{10}$ are each hydrogen or a lower alkyl or an aryl group or, together with the nitrogen atom to which they are attached, form a heterocyclic group, e.g. a pyrrolidino, piperidino, piperazino or morpholino group. When such a group is separated from the phenyl ring by a methylene or ethylene group, $R^3$ has the formula —$CH_2CONR^9R^{10}$, —$CH_2CH_2CONR^9R^{10}$, —$CH_2SO_2NR^9R^{10}$ or —$CH_2CH_2SO_2NR^9R^{10}$.

When $R^3$ is an acylamino group, it may be derived from the amide of a carboxylic or sulfonic acid, i.e. it may have the formula $R^{11}R^{12}N$— where $R^{11}$ is an acyl group derived from either a carboxylic or a sulfonic acid, $R^{12}$ is hydrogen or a lower alkyl group, or $R^{11}$ and $R^{12}$ together with the nitrogen atom form a cyclic imido group. Moreover any such group may be separated from the phenyl ring by a methylene or ethylene group, in which case $R^3$ will have the formula $R^{11}R^{12}NCH_2$— or $R^{11}R^{12}NCH_2CH_2$—.

Thus $R^3$ may be, for example, a formamido, acetamido, propionamido, acrylamido, cyclo-hexane carbonamido, benzamido, furamido, phenyl acetamido, methane sulfonamido, benzene sulfonamido group, or a substituted derivative thereof, e.g. a chloroacetamido, trifluoracetamido, glycolamido, phenoxyacetamido, toluamido, nitro-benzamido, chlorobenzamido or toluene sulfonamido group, or a corresponding amido-methyl or 2-amido-ethyl group, e.g. an acetamido-methyl or 2-acetamido-ethyl group. When $R^{11}R^{12}N$— is a cyclic imido group, it may be derived from an aliphatic or aromatic dicarboxylic acid; thus $R^3$ may be, for example, a succinimido, maleimido or phthalimido group or a corresponding imidomethyl or 2-imido-ethyl group.

When $R^3$ is a ureido group, it may be ureido substituted with one or more lower alkyl groups on one or both of the nitrogen atoms. Thus it may be, for example, a 3-methyl ureido group.

Acids from which pharmaceutically-acceptable addition salts of the compounds of the invention can be prepared are those which form non-toxic addition salts containing pharmaceutically-acceptable anions, such as the hydrochloride, hydrobromide, hydroiodide, sulfate or bisulfate, phosphate or acid phosphate, acetate, maleate, fumarate, lactate, tartrate, citrate, gluconate, saccharate, and p-toluene sulfonate salts.

The compounds of the invention may be prepared in a number of ways: (1) An amine of the formula:

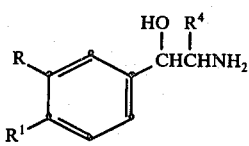
(III)

is reacted with an aldehyde or ketone of the formula:

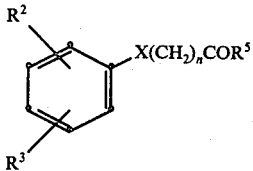
(IV)

to give the corresponding Schiff's base, which is reduced in the presence of a hydrogenation catalyst, e.g. platinum, to a compound of the invention in which $R^6$ is hydrogen and Y represents a hydrogen atom and a hydroxy group.

After filtration and evaporation to dryness the product is isolated by trituration followed by crystallization, or by dissolution in a suitable solvent and precipitation as a salt, e.g. the hydrochloride, maleate, fumarate or oxalate, by addition of the appropriate acid.

(2) A phenacyl halide of the formula:

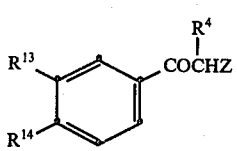
(V)

where Z is halogen and $R^{13}$ and $R^{14}$ are each represent hydrogen or, a group PO—, where P is an easily hydrogenolyzable protecting group, e.g. a benzyl group, at least one of $R^{13}$ and $R^{14}$ being a group PO—, is reacted with an amine of the formula:

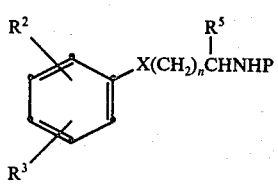
(VI)

to give a compound of the formula:

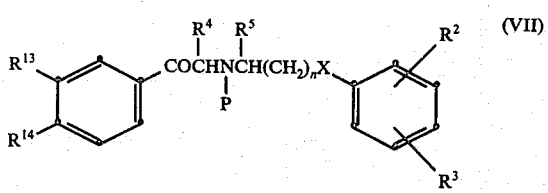
(VII)

To obtain a compound of the invention in which Y represents a hydrogen atom and a hydroxy group and $R^6$ represents hydrogen, the ketonic compound is reduced to the corresponding secondary alcohol and the protecting groups (P) are removed by hydrogenolysis using a catalyst, e.g. palladium. To produce a compound of the invention in which Y represents an oxygen atom and $R^6$ represents hydrogen, the ketonic compound itself is freed of the protecting groups (P) by hydrogenolysis. The methods of isolation and purification are similar to those given for method (1).

(3) An amide of the formula:

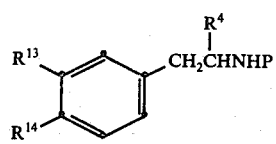
(VIII)

in which $R^{13}$, $R^{14}$ and P are as defined in (2) above, is reacted with a halo-compound of the formula:

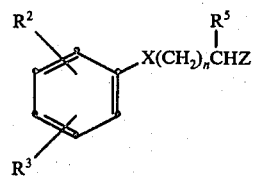
(IX)

in which Z is halogen, to give a compound of the formula:

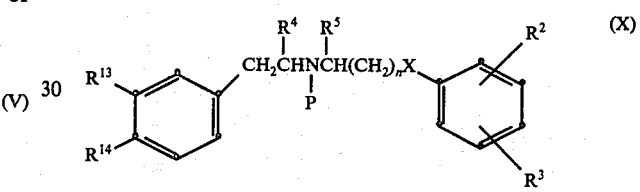
(X)

The protecting groups (P) are then removed by hydrogenolysis as before and the methods of isolation and purification are similar to those given for method (1).

(4) An amine of the formula:

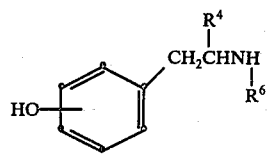
(XI)

in which the single hydroxy group is in either the 3- or the 4- position, is reacted with a halo-compound of the formula (IX) to give a compound of the formula:

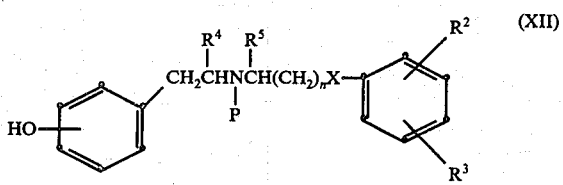
(XII)

The methods of isolation and purification are similar to those given for method (1). Where $R^6$ is hydrogen, an excess amount of the amine is used to prevent excessive formation of the tertiary amine by-product not required.

(5) The compounds of the invention in which $R^3$ represents an acylamino, a lower alkoxy carbonylamino or a ureido group attached directly to the phenyl ring, i.e. groups wherein the free valency is on the nitrogen atom, $R^6$ represents a hydrogen atom, and Y represents a hydrogen atom and a hydroxy group or an oxygen atom, may be prepared from a phenacyl halide of the formula (V) as defined in method (2) and an amine of the formula:

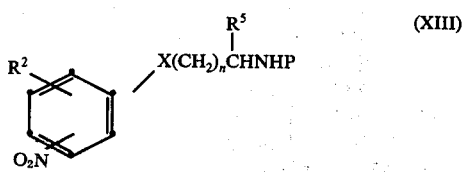 (XIII)

to give a compound of the formula:

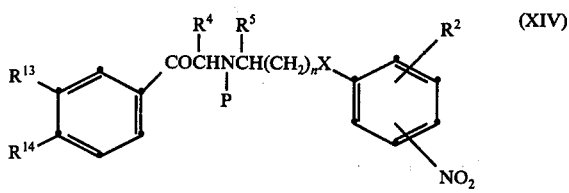 (XIV)

For the preparation of compounds wherein Y represents a hydrogen atom and a hydroxy group, the ketonic compound is then reduced to the corresponding secondary alcohol, whereas for the preparation of compounds wherein Y represents an oxygen atom, this stage is omitted. The nitro group is reduced by hydrogenation in the presence of a catalyst, e.g., Raney nickel, to an amino group to give a compound of the formula:

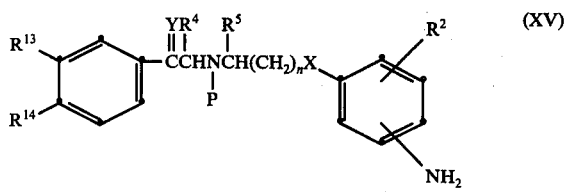 (XV)

in which Y represents a hydrogen atom and a hydroxy group or an oxygen atom. The compound (XV) is then reacted with a suitable reagent for conversion of the amino group to an acylamino group, a lower alkoxycarbonylamino group or a ureido group; e.g. for conversion of the amino group to a formamido, ethoxycarbonylamino or a 3-methyl-ureido group, suitable reagents are formic acid, ethyl chloroformate and methylisocyanate respectively. Finally, the protecting groups (P) are removed by hydrogenolysis using a catalyst, e.g. palladium, to give a compound of the formula (I) wherein $R^3$ represents an acylamino, a lower alkoxycarbonylamino or a ureido group attached directly to the phenyl ring, and Y represents a hydrogen atom and a hydroxy group or an oxygen atom.

(6) The compounds of the invention in which $R^3$ represents an acylamino, a lower alkoxycarbonylamino or a ureido group attached directly to the phenyl ring, and Y represents two hydrogen atoms, may be prepared from an amine of the formula (VIII) as defined in method (3) and a halo-compound of the formula:

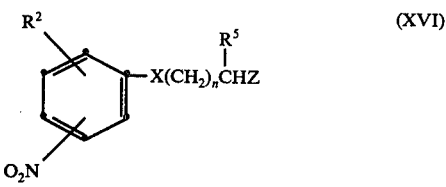 (XVI)

to give a compound of the formula:

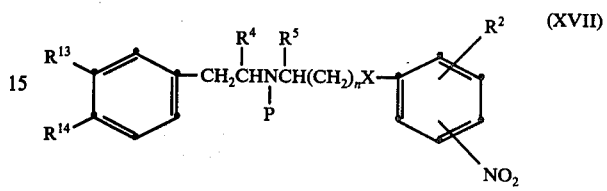 (XVII)

The nitro group is then reduced by hydrogenation in the presence of a catalyst, e.g. Raney nickel, to an amino group to give a compound of the formula:

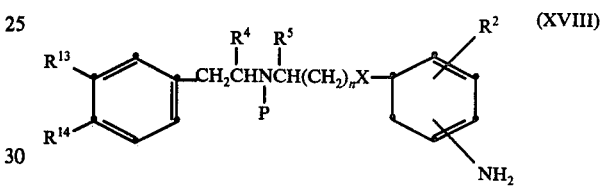 (XVIII)

The compound (XVIII) is then reacted with a suitable reagent for conversion of the amino group to an acylamino, a lower alkoxycarbonylamino or a ureido group such as are exemplified in method (5). Finally, the protecting groups (P) are removed by hydrogenolysis using a catalyst, e.g. palladium.

(7) The compounds of the invention in which $R^6$ represents a lower alkyl group may be prepared by the methods (2), (3), (5) and (6), but with the protecting groups (P) attached to the nitrogen atom in the starting materials (VI), (VIII), (XIII) and (VIII) respectively, replaced by $R^6$.

(8) The aldehyde condensation products of the compounds of the invention may be prepared by reacting a compound of the invention in which $R^4$ and $R^6$ are each hydrogen with an aldehyde of the formula $R^8CHO$, where $R^8$ is hydrogen or a lower alkyl group, in a diluent or solvent, e.g. ethanol, preferably in the presence of an acid catalyst, e.g. hydrochloric or acetic acid, and preferably at an elevated temperature. The water formed in the reaction may be removed by azeotropic distillation by means of an entraining solvent, e.g. benzene, or by dehydrating agent, e.g. anhydrous potassium carbonate.

In the general methods (5) to (8), the methods of isolation and purification are similar to those given for method (1).

Those compounds of the invention in which Y represents a hydrogen atom and a hydroxy group exist in D- and L-optically active isomeric forms and the invention includes these forms as well as the racemic mixtures. Method (1) described above may be used to prepare the optically active isomers by using the appropriately substituted phenyl-ethanolamine enantiomer as starting material, whereas methods (2) and (5) applied to such compounds of the invention will result in the production of a racemic mixture. Alternatively, the racemic product of each of the above methods may be resolved by well-known techniques, e.g. by fractional crystallization of an addition salt formed with an optically active acid.

Compounds in which $R^4$ and/or $R^5$ are other than hydrogen have more than one asymmetric center and exist as two or more racemic pairs of diastereoisomers. In general, the products of the above methods will be a mixture of the pairs of stereoisomers, and these pairs may usually be separated from each other by physical methods, e.g. by fractional crystallization or chromatography of the free bases or suitable salts. The invention includes the separated pairs, as well as mixtures thereof, as racemic mixtures or as separated D- and L-forms.

The activity of compounds of the invention as β-adrenergic stimulants for the heart has been shown by their effectiveness in one or more of the following tests: (a) increasing the force of contraction of the isolated electrically driven guinea-pig left atrium, and of isolated electrically driven cat papillary muscle; (b) increasing the force and/or rate of contraction of spontaneously beating guinea-pig atria; (c) increasing cardiac output in the anaesthetized cat with an implanted left ventricular catheter; (d) increasing cardiac output in the conscious dog with an implanted left ventricular catheter.

In test (a), the increased contractility of the muscle in response to the test compound is measured in two animal species (guinea-pig and cat). The experiments are then repeated in the presence of a β-receptor blocking agent and on reserpinized atria to determine whether the test compound is a directly acting β-receptor agonist.

In test (b) any selective action of compounds of the invention is shown compared with the catecholamines, noradrenaline and adrenaline, i.e. whether or not they increase the force of atrial contraction to a greater extent than the rate.

In test (c) the inotropic action of the test compounds following intravenous administration is measured in the anaesthetized cat. The peripheral effects of the compounds (e.g. effect on blood pressure) are also measured in this preparation.

In test (d) the inotropic action of the test compound following oral administration to a dog with an implanted left ventricular catheter is measured.

By virtue of their performance in tests (a) to (d), the preferred compounds are to be found generally in those compounds of the invention in which R represents hydrogen, $R^1$ represents a hydroxy group, $R^6$ represents hydrogen, X represents oxygen, Y represents a hydrogen atom and a hydroxy group, and n is 1. More particularly, the preferred compounds have the above features and in addition $R^4$ and $R^5$ each represent hydrogen. Particularly preferred compounds are those which show good potency of activity in test (a), and which show a good inotropic response and good duration of action accompanied by only a slight increase in heart rate in test (c), and are specifically DL-2-[2-(4-carbamoylphenoxy)ethylamino]-1-(4-hydroxyphenyl) ethanol, DL-1-(4-hydroxyphenyl)-2-[2-(4-{3-methylureido}phenoxy)ethylamino] ethanol and DL-2-[2-(4-formamidophenoxy)ethylamino]-1-(4-hydroxyphenyl)ethanol. Two more compounds, DL-2-[2-(4-carbamoylmethylphenoxy)ethylamino]-1-(4-hydroxyphenyl)ethanol and DL-2-[2-(4-acetamidophenoxy)ethylamino]-1-(4-hydroxyphenyl)ethanol hydrochloride show good potency of activity in test (a), but are inferior to the three particularly preferred compounds in test (c).

The compounds of the invention can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally, for example, intramuscularly or subcutaneously. For parenteral administration, they are best used in the form of a sterile aqueous solution which may contain other solutes, for example, enough salts or glucose to make the solution isotonic.

In general, the compounds of the invention are administered in dosages of from about 0.5 to about 20 mg./per kg. of body weight per day taken orally in three of four divided doses. Dosages for intravenous administration are about one-tenth of the above dose in a single dose per day.

EXAMPLE I

A mixture of DL-octopamine (4.6 g.), 4-carbamoylphenoxy acetone (5.8 g.) and ethanol (150 ml.) was boiled under reflux for 8 hours in the presence of molecular sieves, then hydrogenated over platinum oxide at 50 p.s.i. and 50° C. Filtration and evaporation in vacuo of the filtrate gave a viscous oil which was triturated with ether to provide a semi-solid material. This material was then triturated with ethanol and the residual white solid crystallized from aqueous dimethylformamide to afford DL-2-[2-(4-carbamoyl-phenoxy)-1-methylethylamino]-1-(4-hydroxyphenyl)ethanol hemihydrate (2.0 g.), m.p. 195°–198° C.

Analysis: Calc'd. for $C_{18}H_{22}N_2O_4.0.5H_2O$: C, 63.70; H, 6.83; N, 8.26%: Found: C, 63.98; H, 6.37; N, 8.27%.

EXAMPLE II

Also prepared by the method described in Example I from DL-octopamine and 2-carbamoyl-4-methylphenoxy acetone was DL-2-[2-(2-carbamoyl-4-methylphenoxy)-1-methylethylamino]-1-(4-hydroxyphenyl)ethanol, isolated as the oxalate, m.p. 175°–6° C.

Analysis: Calc'd. for $C_{19}H_{24}N_2O_4.C_2H_2O_4$: C, 58.06; H, 6.03; N, 6.45%: Found: C, 58.23; H, 6.43; N, 6.65%.

EXAMPLE III

A stirred mixture of 4-benzyloxyphenacyl bromide (18.3 g.), N-[2-(4-carbamoylmethylphenoxy)ethyl]benzylamine (17.0 g.), anhydrous sodium carbonate (6.4 g.) and ethanol (200 ml.) was boiled under reflux for 1 hour, then allowed to cool and filtered. Evaporation in vacuo of the filtrate afforded an oil which could not be induced to solidify. It was thus stirred with a mixture of sodium borohydride (2.4 g.), ethanol (100 ml.) and 1,4-dioxane (100 ml.) for 18 hours at room temperature. The resulting mixture was acidified with 50% aqueous acetic acid then evaporated in vacuo to provide an oil which on trituration with 10% aqueous sodium carbonate solution, gave a white powder (17.3 g.). Crystallization of a sample (2.0 g.) from methanol furnished DL-2-[N-benzyl-2-(4-carbamoylmethylphenoxy)ethylamino]-1-(4-benzyloxyphenyl)ethanol hydrate (0.9 g.), m.p. 105°–107° C.

Analysis: Calc'd. for $C_{32}H_{36}N_2O_5$: C, 72.70; H, 6.86; N, 5.30%: Found: C, 72.99; H, 6.86; N, 5.31%.

The previous product (15.3 g.) was hydrogenated over 10% palladium/charcoal (1.5 g.) in 50% aqueous acetic acid solution (100 ml.) in a Parr hydrogenator at 15 p.s.i. and room temperature. Filtration of the resulting mixture followed by evaporation in vacuo of the filtrate gave an oil which was neutralized by addition of 10% aqueous sodium carbonate solution. The aqueous phase was decanted and the residual oil treated with water in which it rapidly dissolved. On standing, the latter solution deposited a white solid; several more crops were obtained by concentration of this solution, and also from the decantate, to give a total yield of 6.9 g. Crystallization from methanol afforded DL-2-[2-(4-carbamoylmethylphenoxy)ethylamino]-1-(4-hydroxyphenyl)ethanol (4.1 g.) m.p. 160°–161° C.

Analysis: Calc'd. for $C_{18}H_{22}N_2O_4$: C, 65.44; H, 6.71; N, 8.48%: Found: C, 65.85 H, 6.72; N, 8.36%.

EXAMPLE IV (A) A stirred mixture of 3-benzyloxyphenacyl bromide (15.25 g.), N-[2-(4-sulfamoylphenoxy)ethyl]benzylamine (15.3 g.), anhydrous sodium carbonate (5.3 g.) and ethanol (200 ml.) was boiled under reflux for 1 hour, then allowed to cool and filtered to remove the sediment of inorganic salts. Evaporation in vacuo of the filtrate afforded a yellow solid, which was distributed between water (500 ml.) and chloroform (400 ml.). The layers, which initially coalesced into an emulsion, were clarified by filtration through an anhydrous sodium carbonate pad. The chloroform layer was separated, dried over anhydrous magnesium sulfate and evaporated in vacuo to afford a viscous yellow oil, which was found to be very impure from thin layer chromatography evidence. Addition of diethyl ether, chilling, evaporation of the solvent and standing at room temperature eventually solidified the oil to a cake, which was crushed, washed with diethyl ether and dried, providing a cream-colored powder, yield 15.9 g., m.p. 110°–115° C.

(B) A solution of the crude product of (A) (13.25 g.) in 1:1 ethanol: 1,4-dioxane (100 ml.) was added over one minute to a stirred suspension of sodium borohydride (0.95 g.) in ethanol (100 ml.) at room temperature, and the mixture was stirred for a further 21 hours. The resulting mixture was then acidified with glacial acetic acid, the whole than being evaporated in vacuo to a tarry material to which was added aqueous sodium carbonate solution. Water was added, and the resulting solution extracted with chloroform. The layers, which initially coalesced into an emulsion, were clarified by filtration through diatomaceous earth. The chloroform layer was separated, dried over anhydrous magnesium sulfate and evaporated in vacuo to afford an oil which could not be induced to solidify despite trituration in 40°–60° C. petrol ether and diethyl ether with chilling.

(C) The crude product of the previous stage (13.2 g.) was hydrogenated over 10% palladium/charcoal (1.5 g.) in glacial acetic acid (90 ml.) in a Parr hydrogenator at 15 p.s.i.. and room temperature. Filtration of the resulting mixture followed by evaporation in vacuo of the filtrate gave an oil which was dissolved in ethanol (200 ml.). To the ethanolic solution was added concentrated hydrochloric acid which resulted in precipitation of a white crystalline solid, which, after concentration by evaporation of the suspension to a volume of 50 ml., was collected by filtration and dried. It was then dissolved in a boiling ethanol/methanol mixture, the solution filtered, and the filtrate chilled and diluted with diethyl ether. The resultant precipitate of white powder was collected by filtration and dried. The product, DL-2-[2-(4-sulfamoylphenoxy)ethylamino]-1-(4-hydroxyphenyl)ethanol hydrochloride (5.95 g.) melted at 184° C. with decomposition.

Analysis: Calc'd. for $C_{16}H_{20}N_2O_5S\cdot HCL$: C, 49.42; H, 5.44; N, 7.21%: Found: C, 49.33; H, 5.58; N, 7.14%.

The following compounds have been prepared, using the method of Examples III and IV, from the appropriate starting materials.

The compounds of Examples XV, XVI and XVII were produced according to the method of Examples III and IV but omitting the sodium borohydride reduction and effecting the hydrogenation of the carbonyl intermediate at a pressure of about 1000 p.s.i, and at room temperature in the presence of palladium/charcoal catalyst.

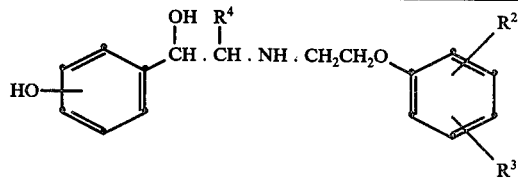

| EXAMPLE | $R^2$ | $R^3$ | $R^4$ | Position of HO— | Salt/Free Base m.p. ° C | Analysis % (calculated in brackets) | | |
|---|---|---|---|---|---|---|---|---|
| | | | | | | C | H | N |
| V | H | 4-CONH$_2$ | H | 4- | Free base 193–5° | 64.56 (64.54 | 6.27 6.37 | 8.86 8.86) |
| VI | H | 4-NHCOCH$_3$ | CH$_3$ | 4- | Hydrochloride 213–6° * | 59.59 (59.92 | 6.47 6.62 | 7.39 7.36) |
| VII | H | 4-CONH$_2$ | CH$_3$ | 4- | Free base 193–6° * | 65.41 (65.44 | 6.63 6.71 | 8.25 8.48) |
| VIII | H | 4-NHCOCH$_3$ | H | 3- | Hydrochloride sesquihydrate 196–8° | 54.56 (54.89 | 6.01 6.64 | 7.25 7.11) |
| IX | H | 4-NHCOCH$_3$ | H | 4- | Hydrochloride 211–2° | 58.52 (58.92 | 6.46 6.32 | 7.68 7.64) |
| X | H | 4-CH$_2$CONH$_2$ | CH$_3$ | 4- | Free base 132–4° * | 66.34 (66.26 | 7.21 7.02 | 7.88 8.13) |
| XI | H | 4-NHCOCH$_2$CH$_3$ | H | 4- | Hydrochloride 192–3° | 59.68 (59.90 | 6.59 6.61 | 7.31 7.35) |
| XII | 4-CH$_3$ | 2-CONH$_2$ | H | 4- | Hydrochloride 160–2° | 58.88 (58.94 | 6.43 6.32 | 7.77 7.64) |

-continued

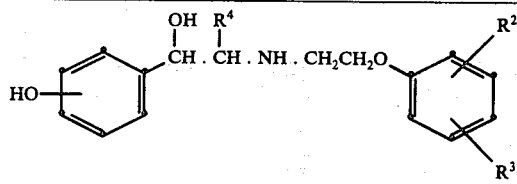

| EXAMPLE | R² | R³ | R⁴ | Position of HO— | Salt/Free Base m.p. °C | Analysis % (calculated in brackets) | | |
|---------|----|----|----|----|----|----|----|----|
| | | | | | | C | H | N |
| XIII | H | 4-NHSO₂CH₃ | H | 4- | Free base 151–3° | 56.08 (55.72 | 5.85 6.05 | 7.48 7.64) |
| XIV | H | 2-NHCOCH₃ | H | 4- | Acetate 166–7° | 61.77 (61.52 | 6.61 6.71 | 7.14 7.18) |
| XV | H | 4-CONH₂ | CH₃ | 4- | Free base 202–4° ** | 65.58 (65.44 | 6.74 6.71 | 8.28 8.48) |
| XVI | H | 4-NHCOCH₃ | CH₃ | 4- | Free base 169–170° ** | 66.43 (66.26 | 7.03 7.02 | 8.01 8.13) |
| XVII | H | 4-CH₂CONH₂ | CH₃ | 4- | Free base 162–4° ** | 66.36 (66.26 | 6.98 7.02 | 8.19 8.13) |
| XVIII | H | 4-CH₂NHCOCH₃ | H | 4- | Free base 147.5–148.5° | 66.13 (66.26 | 7.06 7.02 | 7.84 8.13) |

* threo isomers
** erythro isomers

EXAMPLE XIX

A mixture of 3,4-dibenzyloxyphenacyl bromide (8.2 g.), N-[2-(4-carbamoxylphenoxy)ethyl]benzylamine (5.4 g.) anhydrous sodium carbonate (2.1 g.) and ethanol (250 ml.) was boiled under reflux for 3 hours, then filtered hot to remove the inorganic sediment and cooled to 0° C. The resultant precipitated solid was collected by filtration, washed with diethyl ether and dried. The product, N-benzyl-N-(3,4-dibenzyloxybenzoyl)methyl-2-(4-carbamoylphenoxy)ethylamine (11.0 g.) melted at 140°–2° C.

Analysis: Calc'd. for C₃₈H₃₆N₂O₅.0.5H₂O: C, 74.88; H, 6.1; N, 4.60%. Found: C, 75.83; H, 5.87; N, 4.38%.

Sodium borohydride (4.0 g.) was dissolved in the minimum volume of water and 2 drops of 5N sodium hydroxide solution were added. The solution was added to a suspension of the previous product (10.5 g.) in ethanol (300 ml.) and the mixture stirred for 3 hours at room temperature, then gently warmed on a steam bath to achieve complete solution, and cooled again, stirring then being continued at room temperature for a further 36 hours. The solution was acidified by addition of a few drops of glacial acetic acid and the volume of the suspension reduced by one half. Water (300 ml.) was added and the solid collected by filtration, washed in boiling water and dried to afford DL-2-[N-benzyl-2-(4-carbamoylphenoxy)ethylamino]-1-(3,4-dibenzyloxyphenyl)ethanol (10.1 g.), m.p. 110°–1° C.

Analysis: Calc'd. for C₃₈H₃₈N₂O₅.0.5H₂O: C, 74.60; H, 6.43; N, 4.58%. Found: C, 74.61; H, 5.80; N, 4.32%.

The previous product (6.0 g) was hydrogenated over 10% palladium/charcoal (600 mg.) in 50% aqueous acetic acid solution (60 ml.) in a Parr hydrogenator at 15. p.s.i. and room temperature. Filtration of the resulting mixture followed by evaporation in vacuo of the filtrate at less than 40° C. gave a brown syrup. Addition of an isopropanol/methanol mixture gave a solution and a black solid. The latter was removed by filtration and to the filtrate was added ethereal hydrogen chloride, which produced a gum. Decantation followed by trituration of the gum in methanol afforded a pink solid A (0.4 g.). The decanted isopropanol/methanol/diethyl ether solution was concentrated by evaporation in vacuo, which resulted in precipitation of some more pink solid B (1.3 g.). The filtrates from the collections of solids A and B were combined and treated with a small volume of diethyl ether. Cooling of this solution at 0° C. produced a third crop of crystals, solid C (0.2 g.). Solids A, B and C were combined and dissolved in the minimum volume of methanol, to which was added an approximately equal volume of isopropanol. The solution was concentrated by evaporation until such time as formation of crystals was first observed, after which the solution was cooled at 0° C. during which time more crystallization occurred. The product, collected by filtration and dried, consisted of DL-2-[2-(4-carbamoylphenoxyethylamino]-1-(3,4-dihydroxyphenyl)ethanol hydrochloride (1.05 g.), m.p. 184° C. with decomposition.

Analysis: Calc'd. for C₁₇H₂₀N₂O₅.HCl: C, 55.36; H, 5.74; N, 7.60%. Found: C, 54.98; H, 5.87; N, 7.34%.

EXAMPLE XX

A mixture of 3,4-dibenzyloxyphenacyl bromide (32.8 g.), N-[2-(4-acetamidophenoxy)ethyl]benzylamine (22.8 g.), anhydrous sodium carbonate (8.4 g.) and ethanol (1 liter) was boiled under reflux for 2 hours, then filtered hot to remove the inorganic sediment and evaporated in vacuo to afford a thick syrup. The latter was dissolved in hot isopropanol and the solution cooled, the precipitated solid then being collected by filtration. To a hot solution of the solid in fresh isopropanol were added a few milliliters of ethyl acetate, and the solution was then allowed to cool to room temperature. The crystallized solid was collected by filtration, washed in diethyl ether and dried. Recrystallization from an isopropanol-/ethyl acetate mixture afforded N-benzyl-N-(3,4-dibenzyloxybenzoyl)methyl-2-(4-acetamidophenoxy)ethylamine (32.8 g.), m.p. 104°–6° C.

Analysis: Calc'd. for C₃₉H₃₈N₂O₅: C, 76.20; H, 6.23; N, 4.56%. Found: C, 75.93; H, 6.28; N, 4.13%.

Sodium borohydride (12.0 g.) was dissolved in water (40 ml.) and 8 drops of 5N sodium hydroxide solution were added. The solution was added to a suspension of the previous product (32.8 g) in ethanol (800 ml.) and the mixture gently warmed on a steam bath to achieve complete solution. After removal of the steam bath, the solution was stirred for 10 minutes and poured into water containing a little acetic acid, which resulted in the precipitation of a gummy solid. The latter was extracted into chloroform and the chloroform solution separated and evaporated down in vacuo to give a syrup (20.4 g.), which consisted of crude DL-2-[N-benzyl-2-(4-acetamidophenoxy)ethylamino]-1-(3,4-dibenzyloxyphenyl)ethanol.

The previous product (20.0 g.) was hydrogenated over 10% palladium/charcoal (2.0 g.) in 50% aqueous acetic acid solution (200 ml.) in a Parr hydrogenator at 15 p.s.i. and room temperature. Filtration of the resulting mixture followed by evaporation in vacuo of the filtrate at less than 40° C. gave a syrup, which was subsequently taken up into toluene and the solution evaporated down, this process being repeated until the residue consisted of a pink solid. The latter was dissolved in hot methanol and isopropanol added to the solution. After removal of excess methanol by evaporation in vacuo, a precipitate formed, and this was collected by filtration and dried (yield 11.2 g.; m.p. 150° C. with decomposition). Recrystallization from ethanol afforded 7.1 g. of crystalline material, m.p. 165° C. with decomposition. The filtrate from the crystallization in isopropanol/methanol was treated with ethereal hydrogen chloride, which resulted in precipitation of white crystals (4.6 g.) of DL-2-[2-(4-acetamidophenoxy)ethylamino]-1-(3,4-dihydroxyphenyl)ethanol hydrochloride hemihydrate, m.p. 176° C. with decomposition.

Analysis: Calc'd. for $C_{18}H_{22}N_2O_5.HCl.0.5H_2O$: C, 55.16; H, 5.92; N, 7.15%. Found: C, 55.27; H, 6.21; N, 6.88%.

EXAMPLE XXI

Also prepared by the method described in Examples XIX and XX from 3,4-dibenzyloxyphenacyl bromide and N-[2-(4-carbamoylmethylphenoxy)ethyl]benzylamine was DL-2-[2-(4-carbamoylmethylphenoxy)ethylamino]-1-(3,4-dihydroxyphenyl) ethanol hydrochloride, m.p. 224°–8° C.

Analysis: Calc'd. for $C_{18}H_{22}N_2O_5HCl$: C, 56.47; H, 6.05; N, 7.32%. Found: C, 56.49; H, 6.04; N, 7.51%.

EXAMPLE XXII

A mixture 3,4-dibenzyloxyphenacyl bromide (32.8 g.), N-[2-(4-carbamoylmethylphenoxy)ethyl]benzylamine (22.8 g.), anhydrous sodium carbonate (8.4 g.) and ethanol (1 liter) was boiled under reflux for 3 hours, then filtered hot to remove the inorganic sediment and evaporated in vacuo to afford a thick syrup. The latter was crystallized upon trituration in diethyl ether and a sample of the resultant solid was recrystallized from ethanol to give N-benzyl-N-(3,4-dibenzyloxybenzoyl)-methyl-2-(4-carbamoylmethylphenoxy)ethylamine, m.p. 99°–101° C.

Analysis: Calc'd. for $C_{39}H_{38}N_2O_5.0.5H_2O$: C, 75.10; H, 6.30; N, 4.49%. Found: C, 75.42; H, 6.22; N, 4.17%.

The previous product (7.0 g.) was hydrogenated over 10% palladium/charcoal (700 mg.) in 50% aqueous acetic acid solution (70 ml) in a Parr hydrogenator at 15 p.s.i. and room temperature. Filtration of the resulting mixture was followed by evaporation in vacuo of the filtrate to dryness, the crude product then being azeotroped in turn with water and toluene. The resulting syrup was dissolved in methanol, and ethereal hydrogen chloride was slowly added to the methanolic solution, yielding a precipitate of fawn crystals (4.0 g) which was subsequently collected by filtration and recrystallized from water with a little concentrated hydrochloric acid added. The crystals were collected by filtration and dried to give 2-(4-carbamoylmethyl-phenoxy)-N-(3,4-dihydroxybenzoyl)methyl ethylamine hydrochloride (3.0 g.), m.p. 240° C. with decomposition.

Analysis: Calc'd. for $C_{18}H_{20}N_2O_5.HCl$: C, 56.78; H, 5.55; N, 7.36%. Found: C, 57.01; H, 5.73; N, 7.22%.

EXAMPLE XXIII

Also prepared by the method described in Example XXII from 3,4-dibenzyloxyphenacyl bromide and N-[2-(2-carbamoyl-4-methylphenoxy)-ethyl]benzylamine was 2-(2-carbamoyl-4-methylphenoxy)-N-(3,4-dihydroxybenzoyl)methyl ethylamine hydrochloride hemihydrate, m.p. 180° C., with decomposition between 218°–223° C.

Analysis: Calc'd. for $C_{18}H_{20}N_2O_5.HCl.0.5H_2O$: C, 55.44; H, 5.69; N, 7.19%. Found: C, 55.62; H, 5.62; N, 7.37%.

EXAMPLE XXIV

A mixture of N-2-(3,4-dibenzyloxyphenyl)ethyl benzylamine (13.6 g.), 2-(4-sulfamoylphenoxy)ethyl chloride (4.8 g.) and dry xylene (50 ml.) was boiled under reflux for 12 hours. The solution was cooled and the precipitated solid removed by filtration, the filtrate then being evaporated in vacuo to dryness and taken up into diethyl ether. Insoluble material was removed from the ethereal solution by filtration, and the filtrate treated with ethereal hydrogen chloride, which resulted in the precipitation of a yellow solid. The latter was collected by filtration and recrystallized from a methanol/isopropanol mixture giving N-[2-(3,4-dibenzyloxyphenyl)ethyl]-N-[2-(4-sulfamoylphenoxy) ethyl] benzylamine hydrochloride (5.8 g.), m.p. 178°–181° C.

Analysis: Calc'd. for $C_{37}H_{38}N_2O_5S.HCl$: C, 67.40; H, 5.96; N, 4.25%. Found: C, 67.62; H, 6.03; N, 4.26%.

The previous product (5.7 g.) was hydrogenated over 10% palladium/charcoal in glacial acetic acid in a Parr hydrogenator at 15 p.s.i. and room temperature. The catalyst was removed by filtration and the filtrate evaporated in vacuo to a gum, which was triturated in a little acetone. The resulting grey solid was filtered off, and recrystallized from 5N hydrochloric acid giving N-[2-(3,4-dihydroxyphenyl)ethyl]-2-(4-sulfamoylphenoxy)ethylamine hydrochloride as pale mauve crystals, m.p. 245°–7° C.

Analysis: Calc'd. for $C_{16}H_{20}N_2O_5S.HCl$: C, 49.40; H, 5.44; N, 7.20%. Found: C, 49.39; H, 5.41; N 7.31%.

The following compounds have been prepared, using the method of Example XXIV from the appropriate starting materials.

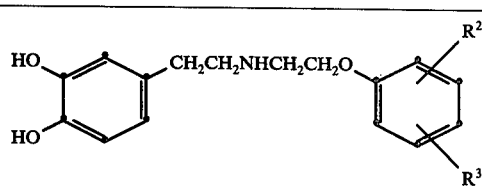

| Ex. | $R^2$ | $R^3$ | Salt m.p. °C | Analysis % (calculated in brackets) | | |
|---|---|---|---|---|---|---|
| | | | | C | H | N |
| XXV | 4-CH$_3$ | 2-CONH$_2$ | Hydro-chloride 200–202° | 58.66 (58.93 | 6.33 6.32 | 7.47 7.64) |
| XXVI | H | 4-CONH$_2$ | Hydro-chloride | 57.46 (57.87 | 5.90 5.71 | 8.02 7.94 |

-continued

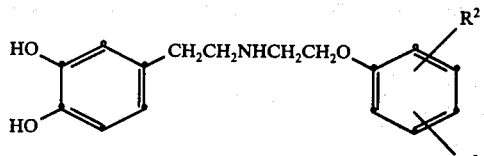

| Ex. | R² | R³ | Salt m.p. °C | Analysis % (calculated in brackets) | | |
|-----|----|----|--------------|----|----|----|
| | | | | C | H | N |
| | | | 241-3° | | | |

EXAMPLE XXVII

A mixture of N-2-(3,4-dibenzyloxyphenyl)ethyl benzylamine (12.0 g.), 2-(4-acetamidophenoxy)ethyl chloride (3.1 g.) and dry dimethylformamide (10 ml.) was boiled under reflux for 10 hours. The solution was cooled, more dimethylformamide (15 ml.) added, and the precipitated solid removed by filtration. The filtrate was evaporated in vacuo to dryness and the resultant solid stirred in chloroform, after which undissolved material was removed by filtration and the filtrate was evaporated in vacuo to dryness to give the crude product, N-[2-(3,4-dibenzyloxyphenyl)ethyl]-N-[2-(4-acetamidophenoxy) ethyl]benzylamine.

The previous product was hydrogenated over 10% palladium/charcoal in aqueous acetic acid with a few drops of concentrated hydrochloric acid added in a Parr hydrogenator at 15 p.s.i. and room temperature. The catalyst was removed by filtration and the filtrate evaporated in vacuo to a gummy solid. The latter was crystallized from dilute hydrochloric acid, giving N-[2-(3,4-dihydroxyphenyl)ethyl]-2-(4-acetamidophenoxy)ethylamine hydrochloride (2.5 g.) m.p. 219°–221° C.

Analysis: Calc'd. for $C_{18}H_{22}N_2O_4 \cdot HCl$: C, 58.93; H, 6.32; N, 7.64%. Found: C, 58.97; H, 6.26; N, 7.90%.

The following compounds have been prepared, using the method of Example XXVII, from the appropriate starting materials.

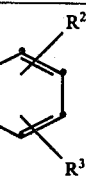

| EXAMPLE | R² | R³ | Salt m.p. °C. | Analysis % (calculated in brackets) | | |
|---------|----|----|---------------|----|----|----|
| | | | | C | H | N |
| XXVIII | 2-OCH₃ | 4-CONH₂ | Hydrochloride 0.25 hydrate 168–171° | 55.80 (55.82 | 6.22 6.05 | 7.09 7.23) |
| XXIX | H | 3-CONH₂ | Hydrochloride 211–4° | 57.97 (57.87 | 5.92 5.71 | 7.79 7.94) |
| XXX | H | 4-CH₂CONH₂ | Hydrochloride 219–221° | 58.83 (58.93 | 6.35 6.32 | 7.45 7.64) |

EXAMPLE XXXI

A mixture of 2-(4-hydroxyphenyl)ethylamine (5.6 g.), 2-(4-carbamoylphenoxy) ethyl chloride (4.0 g.) and dimethylformamide (25 ml.) was heated at 140° C for 4 hours. After cooling to room temperature, the mixture was poured into water and the resultant precipitated solid was collected by filtration, washed in turn with water, acetone and diethyl ether, and finally dried. The product, N-[2-(4-hydroxyphenyl)ethyl]-2-(4-carbamoylphenoxy)ethylamine hydrochloride melted with decomposition at 284° C.

Analysis: Calc'd. for $C_{17}H_{20}N_2O_3 \cdot HCl$: C, 60.62; H, 6.28; N, 8.32%. Found: C, 60.41; H, 6.33; N, 8.56%.

EXAMPLE XXXII

Also prepared by the method described in Example XXXI from 2-(4-hydroxyphenyl)ethylamine and 2-(4-acetamidophenoxy)ethyl chloride was N-[2-(4-hydroxyphenyl)ethyl]-2-(4-acetamidophenoxy)ethylamine hydrochloride, m.p. 275°–7° C.

Analysis: Calc'd. for $C_{18}H_{22}N_2O_3 \cdot HCl$: C, 61.62; H, 6.61; N, 7.99%. Found: C, 61.51; H, 6.64; N, 8.01%.

EXAMPLE XXXIII (A) A stirred suspension of 4-benzyloxyphenacyl bromide (30.5 g.) N-benzyl-2-(4-nitrophenoxy)ethylamine hydrochloride (30.85 g.) and anhydrous sodium carbonate (21.2 g.) in ethanol (300 ml.) was boiled under reflux for 1½ hours. The mixture was then filtered while still hot to remove sodium salts and the ethanolic filtrate evaporated in vacuo to a brown oil (48.7 g.), consisting of crude N-benzyl-N-(4-benzyloxybenzoyl)methyl-2-(4-nitrophenoxy) ethylamine.

(B) Addition of 1,4-dioxane (150 ml.) to the product of (A) caused precipitation of some white solid. The latter was removed by filtration, and the dark brown filtrate added over 5 minutes to a stirred suspension of sodium borohydride (3.8 g.) in ethanol (100 ml.) at room temperature. Stirring was continued for 20 hours, after which the mixture was acidified with glacial acetic acid, diluted by addition of water and basified with aqueous sodium carbonate solution. The solution was extracted with chloroform (2 × 200 ml.) and the chloroform solutions separated, combined, dried over anhydrous magnesium sulfate and evaporated in vacuo to a brown oil (41.8 g.), consisting of crude DL-2-[N-benzyl-2-(4-nitrophenoxy)ethylamino]-1-(4-benzyloxyphenyl)ethanol.

(C) The crude product of (B), dissolved in a mixture of ethanol (150 ml.) and 1,4-dioxane (50 ml.), was submitted to hydrogenation at 50 p.s.i. and room temperature in the presence of Raney nickel catalyst. Removal of catalyst by filtration followed by evaporation of the filtrate in vacuo yielded crude DL-2-[N-benzyl-2-(4-aminophenoxy)ethylamino]-1-(4-benzyloxyphenyl)ethanol (37.85 g.) as a dark brown tar.

(D) A solution of methyl isocyanate (2.85 g.) in chloroform (25 ml.) was added over ½ minute to a stirred solution of the product of (C) (23.4 g.) in chloroform (100 ml.). Stirring at room temperature was continued for 2½ hours, after which the solution was evaporated in vacuo to a brown oil. A small sample of the latter yielded a white powder on trituration in 40°-60° petrol ether/diethyl ether/acetonitrile, and the remaining oil was triturated in 40°-60° petrol ether, the mixture being seeded with the foregoing white powder to yield, on standing, a grey solid mass. The latter was crushed and dried, and consisted of crude DL-2-[N-benzyl-2-(4-{3-methylureido} phenoxy)ethylamino]-1-(4-benzoyloxphenyl)ethanol. A small portion was crystallized from acetonitrile to yield crystals, m.p. 113°-116° C.

Analysis: Calc'd. for $C_{32}H_{35}N_3O_4$: C, 73.12; H, 6.71; N, 8.00. Found: C, 72.82; H, 6.59; N, 8.01.

(E) The product of (D) (22.0 g.) dissolved in glacial acetic acid was hydrogenated at 15 p.s.i. and room temperature in the presence of palladium/charcoal catalyst. The catalyst was then removed by filtration and the filtrate treated with concentrated hydrochloric acid (4 ml.~1 equivalent) and evaporated in vacuo to a green oil, which was triturated in diethyl ether/isopropanol to afford a grey tar. Trituration of the latter in acetonitrile (100 ml.) yielded an off-white powder (12.75 g.), which was subsequently dissolved in the minimum amount of warm water, the solution then being basified with aqueous sodium carbonate solution. The aqueous phase was decanted from the precipitated green tar and the latter triturated in turn in diethyl ether and acetone. Successive triturations in fresh amounts of acetonitrile induced solidification to give a cream-colored product (8.45 g.). Crystallization from ethanol/water afforded a cream-colored solid, m.p. 155°-160° C with decomposition. A silver nitrate test on the product indicated the presence of halide and so it was inferred that the product was contaminated with the hydrochloride salt. The aqueous ethanol filtrate was evaporated in vacuo to dryness and the residue combined with the crystallized solid, m.p. 155°-160° C., and the whole treated with warm aqueous saturated sodium carbonate solution to convert it to the free base. Resulting was a fawn powder (6.0 g.) which was crystallized from ethanol to provide fawn crystals (3.7 g.), m.p. 164°-166° C. with decomposition. A final recrystallization from an ethanol/methanol mixture yielded light fawn crystals (2.85 g.) of DL-1-(4-hydroxyphenyl)-2-[2-(4-{3-methylureido} phenoxy)ethylamino]ethanol, m.p. 165°-6° C. with decomposition.

Analysis: Calc'd. for $C_{18}H_{23}N_3O_4$: C, 62.59; H, 6.71; N, 12.17%. Found: C, 62.86; H, 6.80; N, 11.88%.

EXAMPLE XXXIV

Ethyl chloroformate (5.45 g.) was added dropwise over 2-3 minutes to a stirred, warm suspension of DL-2-[N-benzyl-2-(4-aminophenoxy)ethylamino]-1-(4-benzyloxyyphenyl)ethanol (23.4 g) (prepared as described in Example XXXIII (A), (B) and (C)) and anhydrous potassium carbonate (6.9 g.) in ethanol (150 ml.) and the stirred mixture was boiled under reflux for ½ hour. The suspension was then filtered hot to remove off-white solid and the filtrate evaporated in vacuo to a brown tar (27.0 g.) consisting of crude DL-2-[N-benzyl-2-(4-ethoxycarbonylaminophenoxy)ethylamino]-1-(4-benzyloxyphenyl)ethanol hydrochloride.

The previous crude product (27.0 g.) was dissolved in 1:1 glacial acetic acid: water (240 ml.) and hydrogenated at 15 p.s.i. and room temperature over 10% palladium/charcoal catalyst. The catalyst and some accompanying grey solid (independently shown to consist in all probability of the mono-O-benzyl compound mainly) were filtered off, and the yellow aqueous acetic acid filtrate evaporated in vacuo at 40° C. to give a fawn gum, which was triturated in diethyl ether (2 × 250 ml.), the resultant fawn solid then being collected by filtration, dried at 80° C. in vacuo and crystallized from ethanol. The product consisted of off-white crystals (2.25 g.) of DL-2-[2-(4-ethoxycarbonylaminophenoxy)ethylamino]-1-(4-hydroxyphenyl)ethanol hydrochloride, which melted with decomposition in the range 187°-9° C. to an opaque melt, the latter decomposing further with clarification in the range 225°-230° C.

Analysis: Calc'd. for $C_{19}H_{24}N_2O_5 \cdot HCl$: C, 57.49; H, 6.35; N, 7.06%. Found: C, 57.64; H, 6.06; N, 6.94%.

EXAMPLE XXXV

90% Aqueous formic acid solution (4.3 ml.) was added dropwise over 2-3 minutes to a stirred, warm solution of DL-2-[N-benzyl-2-(4-aminophenoxy)ethylamino]-1-(4-benzyloxyphenyl)ethanol (23.4 g.) (prepared as described in Example XXXIII (A), (B) and (C)) in benzene (150 ml.) and the stirred solution was boiled under reflux for 1 hour. Evaporation of the solution, which consisted of two liquid layers, in vacuo afforded a brown oil, and this was then diluted with water (200 ml.) and the pH adjusted to about 6.5 using saturated aqueous sodium carbonate solution. The solution was extracted with chloroform (2 × 100 ml.), the chloroform layers then being separated, dried over anhydrous magnesium sulfate and evaporated in vacuo to afford a brown tar (26.0 g.), which consisted of crude DL-2-[N-benzyl-2-(4-formamidophenoxy) ethylamino]-1-(4-benzyloxyphenyl)ethanol.

The previous crude product (26.0 g.) was dissolved in glacial acetic acid (120 ml.) and hydrogenated at 15 p.s.i. and room temperature over 5% palladium/charcoal catalyst. Evaporation of the filtrate in vacuo at 40° C. from the removal of catalyst yielded a brown tar, which was azeotroped with benzene (2 × 100 ml.). To the resulting brown tar was added water (150 ml) and the pH of the solution, containing suspended white solid, was adjusted from about 4.5 to about 9.5, at which point the solution contained a fawn precipitate. The residual tar was converted to solid by stirring, the whole solid then being collected by filtration and recrystallized twice from ethanol to give fawn crystals (6.55 g.) of DL-1-(4-benzyloxyphenyl)-2-[2-(4-formamidophenoxy)ethylamino]ethanol, m.p. 151.5°-152.5° C.

Analysis: Calc'd. for $C_{24}H_{26}N_2O_4$: C, 70.91; H, 6.45; N, 6.89%, Found: C, 70.56; H, 6.45; N, 6.27%.

The previous product (4.06 g.) was dissolved in glacial acetic acid (60 ml.) and hydrogenated at 15 p.s.i. and room temperature over 10% palladium/charcoal catalyst. Removal of the catalyst by filtration, followed by evaporation in vacuo of the filtrate afforded a brown oil, to which was added saturated aqueous sodium carbonate solution. The resultant gum was solididied by trituration in ethanol, and the solid collected by filtration and crystallized from ethanol to yield off-white crystals (2.3 g.) of DL-2-[2-(4-formamidophenoxy)ethylamino]-1-(4-hydroxyphenyl)ethanol, m.p. 164°-5° C. with decomposition which was found from nuclear magnetic resonance spectroscopy to contain about 10% ethanol.

Analysis: Calc'd. for $C_{17}H_{20}N_2O_4 \cdot 0.1 C_2H_5OH$: C, 64.37; H, 6.47; N, 8.73%, Found: C, 64.69; H, 6.52; N, 8.92%.

What is claimed is:

1. A compound of the formula:

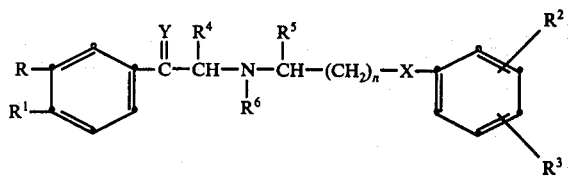

wherein R and $R^1$ are each hydrogen or hydroxy with the proviso that at least one is hydroxy; $R^2$ is hydrogen, alkyl of from 1 to 4 carbon atoms or alkoxy of from 1 to 4 carbon atoms; $R^3$ is formamido, acetamido, propionamido or carbamoyl, any one of which may be separated from the phenyl ring by a methylene or ethylene group; $R^4$, $R^5$ and $R^6$ are each hydrogen or alkyl of from 1 to 4 carbon atoms; X is oxygen, sulfur, imino or a direct link; Y is hydrogen and hydroxy, two hydrogens or oxygen; $n$ is 1 to 3 when X is other than a direct link and is 0 to 4 when X is a direct link; and the pharmaceutically-acceptable acid addition salts.

2. A compound of claim 1 wherein X is oxygen, $n$ is 1 and Y is hydrogen and hydroxy, two hydrogens or oxygen.

3. A compound of claim 1 wherein $R^6$, $R^5$ and $R^4$ are each hydrogen.

4. A compound of claim 1 wherein $R^1$ is hydroxy and R is hydrogen.

5. A compound of claim 1 wherein R and $R^1$ are each hydroxy.

6. A compound of claim 1 wherein R is hydroxy and $R^1$ is hydrogen.

7. A compund of claim 1 wherein $R^3$ is carbamoyl, acetamido, formamido, or proponamido, separated from the phenyl ring by a methylene or ethylene group.

8. A compound of claim 1 wherein $R^2$ is hydrogen.

9. DL-2-[2-(4-(carbamoylphenoxy)ethylamino]-1-(4-hydroxyphenyl)ethanol and its pharmaceutically-acceptable acid addition salts.

10. DL-2-[2-(4-formamidophenoxy)ethylamino]-1-(4-hydroxyphenyl)ethanol and its pharmaceutically-acceptable acid addition salts.

11. DL-2-[2-(4-carbamoylmethylphenoxy)ethylamino]-1-(4-hydroxyphenyl) ethanol and its pharmaceutically-acceptable acid addition salts.

12. DL-2-[2-(4-acetamidophenoxy)ethylamino]-1-(4-hydroxyphenyl)ethanol and its pharmaceutically-acceptable acid addition salts.

* * * * *